(12) United States Patent
Boiman et al.

(10) Patent No.: US 10,695,064 B2
(45) Date of Patent: Jun. 30, 2020

(54) ANASTOMOSIS SUTURING DEVICE

(71) Applicants: Alon Boiman, Tel-Aviv (IL); Adi Borovich, Tel-Aviv (IL); Arie Kalo, Ness Ziona (IL)

(72) Inventors: Alon Boiman, Tel-Aviv (IL); Adi Borovich, Tel-Aviv (IL)

(73) Assignees: Alon Boiman, Tel-Aviv (IL); Adi Borovich, Tel-Aviv (IL); Arie Kalo, Ness Ziona (IL)

( * ) Notice: Subject to any disclaimer, the term of this patent is extended or adjusted under 35 U.S.C. 154(b) by 367 days.

(21) Appl. No.: 15/505,087

(22) PCT Filed: Aug. 17, 2015

(86) PCT No.: PCT/IL2015/050828
§ 371 (c)(1),
(2) Date: Feb. 19, 2017

(87) PCT Pub. No.: WO2016/030877
PCT Pub. Date: Mar. 3, 2016

(65) Prior Publication Data
US 2019/0150928 A1 May 23, 2019

(30) Foreign Application Priority Data
Aug. 24, 2014 (IL) .......................................... 234271

(51) Int. Cl.
*A61B 17/11* (2006.01)
*A61B 17/04* (2006.01)
(Continued)

(52) U.S. Cl.
CPC .......... *A61B 17/11* (2013.01); *A61B 17/0482* (2013.01); *A61B 17/06114* (2013.01); *A61B 17/1114* (2013.01); *A61B 17/30* (2013.01); *A61B 2017/00876* (2013.01); *A61B 2017/0608* (2013.01); *A61B 2017/1107* (2013.01);
(Continued)

(58) Field of Classification Search
CPC . A61B 17/1114; A61B 17/0482; A61B 17/11; A61B 17/1128; A61B 17/0483; A61B 17/0469; A61B 2017/1132; A61B 2017/1107; A61B 2017/0472
See application file for complete search history.

(56) References Cited

U.S. PATENT DOCUMENTS 3,254,650 A * 6/1966 Collito .................... A61B 17/11
606/153
3,561,448 A * 2/1971 Peternel ................. A61B 17/11
606/148

(Continued)

OTHER PUBLICATIONS

Written Opinion in PCT/IL2015/050828, dated Dec. 14, 2015, PCT International Searching Authority, IL.

*Primary Examiner* — Christopher L Templeton
(74) *Attorney, Agent, or Firm* — AlphaPatent Associates, Ltd; Daniel J. Swirsky

(57) ABSTRACT

An anastomosis suturing device includes a dismantable casing, a first tubular section having a proximal section encased in the casing and a distal section insertable in a tubular body of a living creature, and a second tubular section having a proximal section encased in the casing and a distal section insertable in a tubular body of the living creature.

16 Claims, 6 Drawing Sheets

(51) Int. Cl.
*A61B 17/06* (2006.01)
*A61B 17/30* (2006.01)
*A61B 17/00* (2006.01)

(52) U.S. Cl.
CPC ............ *A61B 2017/1132* (2013.01); *A61B 2017/1135* (2013.01)

(56) References Cited

U.S. PATENT DOCUMENTS

| | | | | |
|---|---|---|---|---|
| 4,306,561 A * | 12/1981 | de Medinaceli | ... | A61B 17/1128 606/152 |
| 4,553,543 A * | 11/1985 | Amarasinghe | ......... | A61B 17/04 606/148 |
| 4,873,975 A * | 10/1989 | Walsh | .................... | A61B 17/11 606/153 |
| 4,911,164 A * | 3/1990 | Roth | ................. | A61B 17/0482 606/148 |
| 5,545,171 A * | 8/1996 | Sharkey | ............. | A61B 17/0469 606/139 |
| 5,554,162 A * | 9/1996 | DeLange | ........... | A61B 17/0469 606/153 |
| 5,591,203 A * | 1/1997 | Fahy | ...................... | A61B 17/11 433/159 |
| 5,746,757 A * | 5/1998 | McGuire | ............ | A61B 17/0482 606/139 |
| 5,902,311 A | 5/1999 | Andreas et al. | | |
| 7,001,401 B1 * | 2/2006 | Castaneda | .......... | A61B 17/0469 606/144 |
| 7,608,085 B2 * | 10/2009 | Barrientos | ......... | A61B 17/0482 606/144 |
| 8,221,438 B2 * | 7/2012 | Ortiz | ................ | A61B 17/00234 606/142 |
| 8,911,458 B2 * | 12/2014 | Bassan | ............... | A61B 17/0469 227/175.1 |
| 2005/0209686 A1 * | 9/2005 | Guenst | ................... | A61B 17/30 623/1.23 |

\* cited by examiner

ANASTOMOSIS SUTURING DEVICE

CROSS-REFERENCE TO RELATED APPLICATIONS

This application is a U.S. National Phase Application under 35 U.S.C. 371 of International Application No. PCT/IL2015/050828, which has an international filing date of Aug. 17, 2015, and which claims the priority benefit of Israel Patent Application No. 234271 filed Aug. 24, 2014, which is incorporated herein by reference in its entirety.

FIELD AND BACKGROUND OF THE INVENTION

The present invention, in some embodiments thereof, relates to anastomosis devices and, more particularly, but not exclusively, to a suturing device for use in an anastomosis.

An anastomosis is the term generally used in medicine to refer to the connection of two tubular bodies, for example two blood vessels or two blood vessel sections, or two intestinal sections. They are usually applied to, although not limited to, connect tubular organs in the circulatory system such as arteries and veins; in the gastrointestinal tract such as the esophagus, the small and large intestines, and the bile duct; and in the urinary tract to connect the bladder to the urethra. One common method of connection includes manually suturing the two tubular bodies together. Other known methods include use of mechanical staples or use of a bio-compatible/bio-degradable glue to make the connection.

There are several types of anastomosis, end-to-end, end-to-side, and side-to-side. In the end-to-end anastomosis, an end of a first tubular body is connected to the end of a second tubular body thereby allowing continuity in the flow of blood or other bodily fluids through the joined tubular bodies. In the end-to-side anastomosis, an end of one tubular body is connected to an opening on a wall of a second tubular body, frequently the opening is created through a neostomy procedure where the opening may be artificially created. In the side-to-side anastomosis, a first tubular body is connected to a second tubular body through openings on the walls of both tubular bodies, the openings frequently formed through a neostomy procedure.

SUMMARY OF THE INVENTION

There is provided, in accordance with an embodiment of the present invention, an anastomosis suturing device including a dismantable casing, a first tubular section having a proximal section encased in the casing and a distal section insertable in a tubular body of a living creature, and a second tubular section having a proximal section encased in the casing and a distal section insertable in a tubular body of the living creature.

In accordance with an embodiment of the present invention, the casing includes at least one suture storage cell.

In accordance with an embodiment of the present invention, the casing includes at least one needle activator operable to cause a suture needle to protrude through the first or second tubular body.

In accordance with an embodiment of the present invention, the casing includes at least one needle driver operable to push a needle extender in the first or second tubular section.

In accordance with an embodiment of the present invention, the casing includes a first casing section and a second casing section.

In accordance with an embodiment of the present invention, the first tubular section and the second tubular section each include at least one needle slot to slidingly accommodate a needle extender.

In accordance with an embodiment of the present invention, the at least one needle slot in the first and second needle slot includes a slit to accommodate a suture.

In accordance with an embodiment of the present invention, the first tubular section and the second tubular section each include at least one needle extender to push on a suture needle.

In accordance with an embodiment of the present invention, the first tubular section and the second tubular section each include at least one needle opening to allow protruding of a suture needle.

In accordance with an embodiment of the present invention, the first tubular section and the second tubular section each include at least one suture needle.

In accordance with an embodiment of the present invention, the first tubular section and the second tubular section include distal ends having different diameters.

In accordance with an embodiment of the present invention, the first tubular section and the second tubular section include distal ends having same diameters.

In accordance with an embodiment of the present invention, the anastomosis suturing device is configured to be used for an end-to-end anastomosis.

In accordance with an embodiment of the present invention, the end-to-end anastomosis includes two veins.

In accordance with an embodiment of the present invention, the anastomosis suturing device is configured to be used for an end-to-side anastomosis.

In accordance with an embodiment of the present invention, the end-to-side anastomosis includes an artery and a vein.

In accordance with an embodiment of the present invention, the anastomosis suturing device is configured to be used for a side-to-side anastomosis.

BRIEF DESCRIPTION OF THE DRAWINGS

Some embodiments of the invention are herein described, by way of example only, with reference to the accompanying drawings. Details shown are for exemplary purposes and serve to provide a discussion of embodiments of the invention. The description and the drawings may be apparent to those skilled in the art how embodiments of the invention may be practiced.

DETAILED DESCRIPTION

Figure 1:
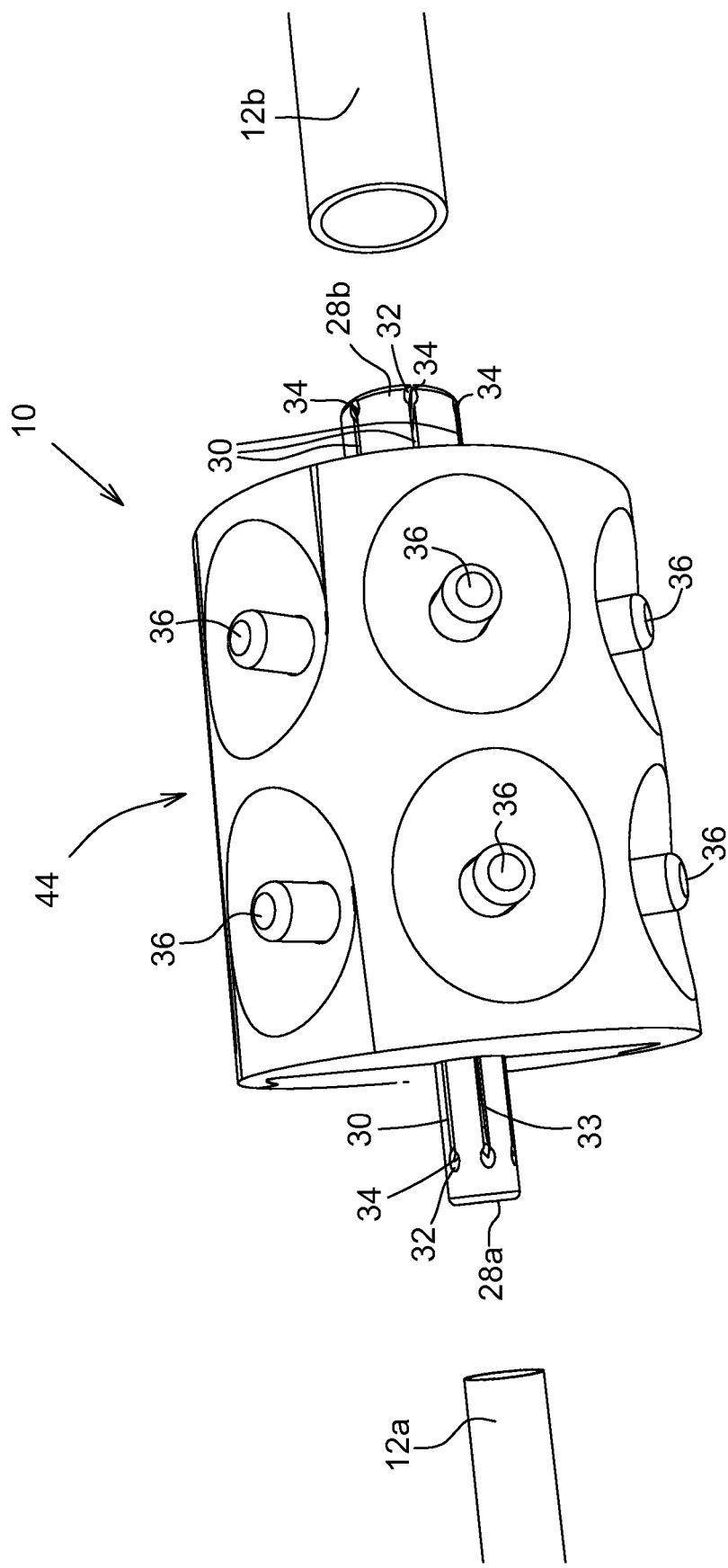
FIG. 1 schematically illustrates a perspective view of an exemplary anastomosis suturing device for use in an end-to-end anastomosis, according to an embodiment of the present invention.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Applicants have realized that the outcome of an anastomosis which includes suturing two bodies together is generally influenced by the skill and experience of the physician carrying out the procedure. Complications may arise as a result of the procedure taking a long time, improper suturing which may result in blood leakage and constrictions, or of excessive handling of the bodies causing them damage.

Applicants have realized that the above complications which may be associated with a level of skill and experience may be substantially eliminated by use of an anastomosis suturing device onto which the two bodies to be connected may be anchored, and which includes a driving mechanism to drive sutures through the anchored bodies. Such an anastomosis suturing device may be particularly advantageous as it may reduce the amount of time generally required to perform the anastomosis while substantially reducing manual handling of the two bodies.

The anastomosis suturing device of the present invention may be used, in some embodiments, for performing an end-to-end anastomosis. In some embodiments, the anastomosis suturing device of the present invention may be used for end-to-side anastomosis. The anastomosis suturing device of the present invention may be used in any one of the circulatory system, the gastrointestinal system, and the urinary tract, although the skilled person in the art may realize that the teachings of the present invention may be applied to other organ systems in human beings as well as in animals. For clarity purposes, reference will be made hereinafter to blood vessels being the tubular bodies, although the skilled person may realize that the invention is not limited to being practiced only to perform anastomosis of blood vessels.

Description of an Exemplary End-to-End Anastomosis Suturing Device

Figure 2:
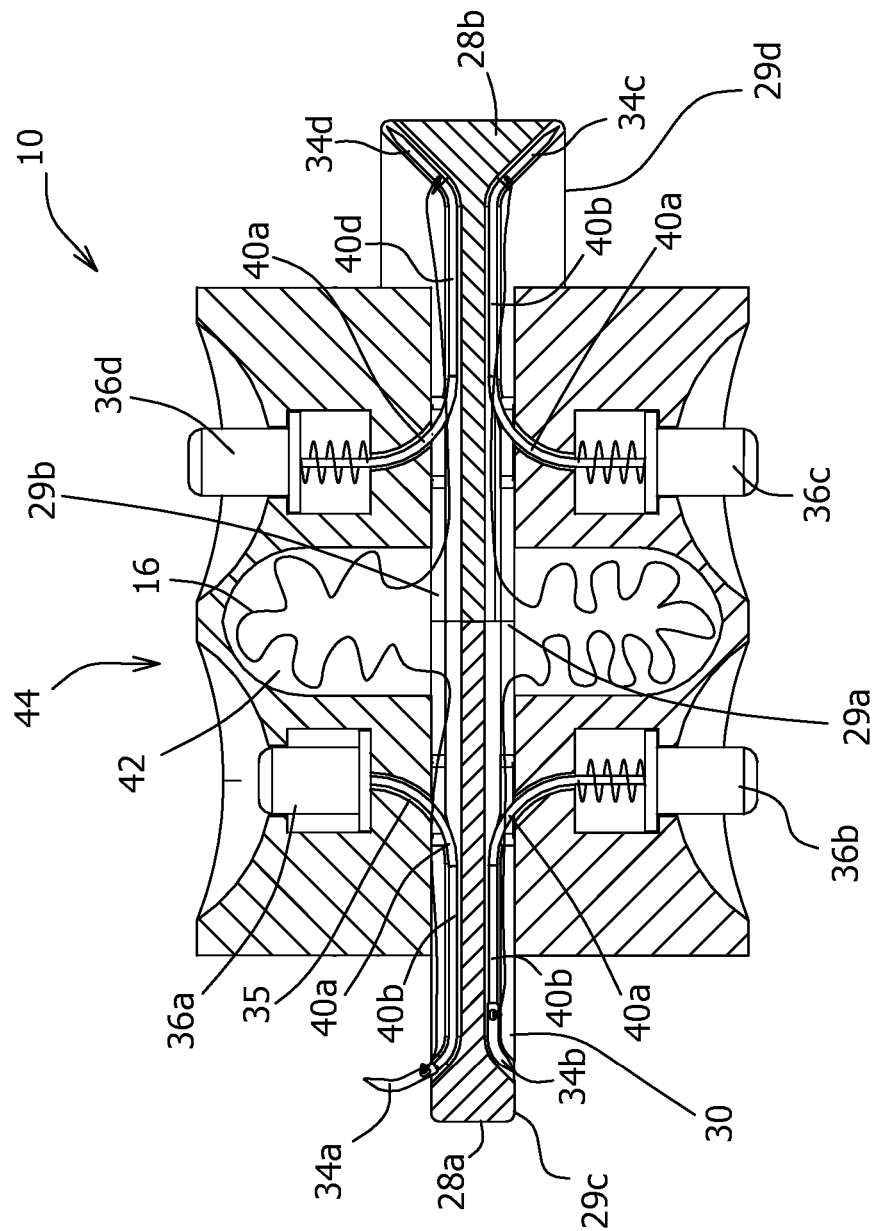
FIG. 2 schematically illustrates a cross-sectional view of the anastomosis suturing device, according to an embodiment of the present invention.

Reference is now made to FIG. 1 which schematically illustrates a perspective view of an exemplary anastomosis suturing device 10 for use in an end-to-end anastomosis, according to an embodiment of the present invention. Reference is also made to FIG. 2 which schematically illustrates a cross-sectional view of anastomosis suturing device 10 and to FIG. 3 which schematically illustrates a perspective view of the anastomosis suturing device partially disassembled, according to an embodiment of the present invention.

Anastomosis suturing device 10 may include a first tubular section 28a and an opposing second tubular section 28b, both tubular sections partially encased within a dismantable casing 44 assembled from two half sections, casing sections 44a and 44b, respectively. Tubular sections 28a and 28b may include proximal sections 29a and 29b, respectively, enclosed in casing 44, each proximal section having a proximal end which may abut one with the other. Tubular sections 28a and 28b may additionally include distal sections 29c and 29d, respectively, which protrude outwards from casing 44 and are insertable into blood vessel sections 12a and 12b. Distal sections 29c and 29d may be of a same diameter, or alternatively, may be of a different diameter to allow their insertion into two blood vessels having different diameters. Blood vessel sections 12a and 12b may be two sections of a same blood vessel which are being joined together by anastomosis suturing device 10, or may be two different blood vessels being joined together.

Tubular sections 28a and 28b may be solid-core tubes or alternatively, hollow-core tubes, or a combination of both. Circumferentially arranged on the surface of distal sections 29c and 29d is a plurality of needle slots 30 extending along a portion of the length of each of the distal sections, each slot terminating in a needle opening 32. Each needle slot 30 may accommodate a suture needle 34 and a needle extender 40 adapted to slide inside the slot and to push the suture needle out through needle opening 32. Each slot 30 may additionally include a lengthwise slit 33 extending along a length of the slot through which may be inserted a suture 16 which is attached to suture needle 34. Tubular sections 28a and 28b may have a same number of needle slots 30, or a different number of needle slots. The plurality of needle slots 30 in each tubular section 28a and 28b may be, for example, 2 needles, 3 needles, 4 needles, 5 needles, 6 needles, 7 needles, 8 needles, 9 needles, 10 needles, or more, with each tubular section having a same number of needles or alternatively, a different number of needles.

Tubular sections 28a and 28b may each be selected having distal sections 29b and 29d, respectively, of a particular diameter corresponding to the diameter of the blood vessel into which it is to be fit. For example, in applications where both blood vessels 12a and 12b are of a same diameter, distal sections 29c and 29d may be selected of a same diameter. In such applications, anastomosis suturing device 10 may be reversibly attached to blood vessels 12a and 12b so that either one of tubular sections 28a or 28b may be fit into blood vessel 12a or 12b. In applications where one blood vessel is of a larger diameter than the other blood vessel, for example 12b has a larger diameter than 12a, then tubular sections 28a and 28b may each be selected having distal sections 29c and 29d of a diameter corresponding to the blood vessel into which it will be fitted (e.g. tubular section 28b having distal section 29d with larger diameter to correspond with the diameter of blood vessel 12b).

Casing 44 may be cylindrically shaped and, as previously mentioned, may be assembled from two dismantable casing sections 44a and 44b. Each casing section 44a and 44b may include one or more suture storage cells 42 to accommodate sutures 16, of which each suture may be connected at one end to a suture needle 34 in a needle slot 30 in tubular section 28a and at an opposing end to a second suture needle 34 in a needle slot 30 in tubular section 28b. For example, referring to FIG. 2, a first suture 16 is shown connected at one end to needle 34a and at an opposing end to needle 34d, and a second suture 16 connected at one end to needle 34b and at an opposing end to needle 34c. Alternatively, suture storage cells 42 may be formed in only one casing section, for example casing section 44a or 44b, or may be formed in voids formed between the two casings when joined together. Casing 44 may be dismantled so that casing section 44a and 44b may be separated. Dismantling may be manually performed by the physician with his fingers, and may include use of a separation tool, to separate casing sections 44a and 44b from one another.

Casing 44 may additionally include for each needle slot 30 in tubular sections 28a and 28b, a needle activator 36 connecting to a needle driver 40a. Each needle driver 40a may be accommodated inside a conduit 35 along which it may be slidingly displaced in a direction towards needle slot 30 when a user (physician) operates activator 36. When displaced towards needle slot 30, needle driver 40a may push on needle extender 40b inside the needle slot, forcing needle 34 to protrude out needle opening 32. Alternatively, needle activator 36 operation may cause more than one needle driver 40a to be slidingly displaced so that more than one needle 34 may protrude out of its needle opening 32. Needle driver 40a may be automatically retrieved into conduit 35 when activator 36 is released.

Needle activator 36 may include a button which may be mechanically depressed by the user to cause needle driver 40a to push on needle extender 40b. Needle activator 36 may include a spring-loaded mechanism which may cause needle driver 40a to slide through conduit 35 towards needle slot 30 and/or to be retrieved into conduit 35 following activation. Alternatively, needle activator 36 and needle driver 40a may be electrically operated, and may include use of a DC power source (battery) in casing 44. Alternatively, needle activator 36 and needle driver 40a may be electromagnetically operated.

Anastomosis suturing device 10 may be fabricated of a metal and/or a plastic material which may be subject to sterilization procedures and other clinical cleansing procedures routinely used for surgical instruments including those used for performing an anastomosis. It may be a reusable device or alternatively, a disposable single-use device.

Anastomosis suturing device 10 may come in various configurations with tubular sections 28a and 28b prefitted in casing 44 and having distal sections 29c and 29d of different diameters (and optionally lengths) for use with different types and/or sizes of blood vessels and with different number of needles. Casing 44 may be preassembled in factoring where casing sections 44a and 44b are joined together with proximal sections 29a and 29b of tubular sections 28a and 28b, respectively, encased inside. Casing 44 may be of a same size or alternatively, may have different sizes which may depend on the type of anastomosis to be performed, the size of the prefitted tubular sections in the casing, and the number of needles which may be used during the procedure. Additionally or alternatively, anastomosis suturing device 10 may be part of a kit which may include a replaceable casing 44 and different size tubular sections 28a and 28b which may be interchanged by the physician depending on the type of anastomosis. In such a kit, casing 44 may be disassembled by the physician (or other suitable user) by separating casing sections 44a and 44b, allowing the selected tubular sections 28a and 28b to be fitted inside. Casing 44 may then be assembled by joining casing sections 44a and 44b so that proximal sections 29a and 29b of tubular sections 28a and 28b are fittedly encased within the casing.

Exemplary Method of Using the End-to-End Anastomosis Suturing Device

Use of anastomosis suturing device 10 may include a physician selecting an anastomosis suturing device which may be prefitted (e.g. during manufacture) with tubular sections 28a and 28b having distal sections 29c and 29d respectively, of preselected diameters. Alternatively to selecting a prefitted anastomosis suturing device, the physician may use an anastomosis suturing device kit, selecting a casing 44 and tubular sections 28a and 28b having distal sections 29c and 29d of the required diameters, and assembling anastomosis suturing device 10 according to physician requirements for performing the anastomosis. Selection of the anastomosis kit parts (i.e. casing 44 and tubular sections 28a and 28b) may be based on medically associated criteria such as the type of anastomosis, size and diameters of blood vessels 12 and 12b, among other criteria.

During the anastomosis procedure, the physician may handle anastomosis suturing device 10 and may connect the device to blood vessels 12a and 12b by inserting distal sections 29c and 29d into the blood vessels. An orientation of anastomosis suturing device 10 may depend on the diameters of distal sections 29c and 29d. That is, the physician may connect tubular section 28a to blood vessel 12a and tubular section 28b to blood vessel 12b if the diameter of distal section 29c corresponds with that of blood vessel 12a and that of distal section 29d with that of blood vessel 12b. Alternatively, the physician may connect tubular section 28a to blood vessel 12b and tubular section 28b to blood vessel 12a if the diameter of distal section 29d corresponds with that of blood vessel 12a and that of distal section 29c with that of blood vessel 12b.

Figure 3:
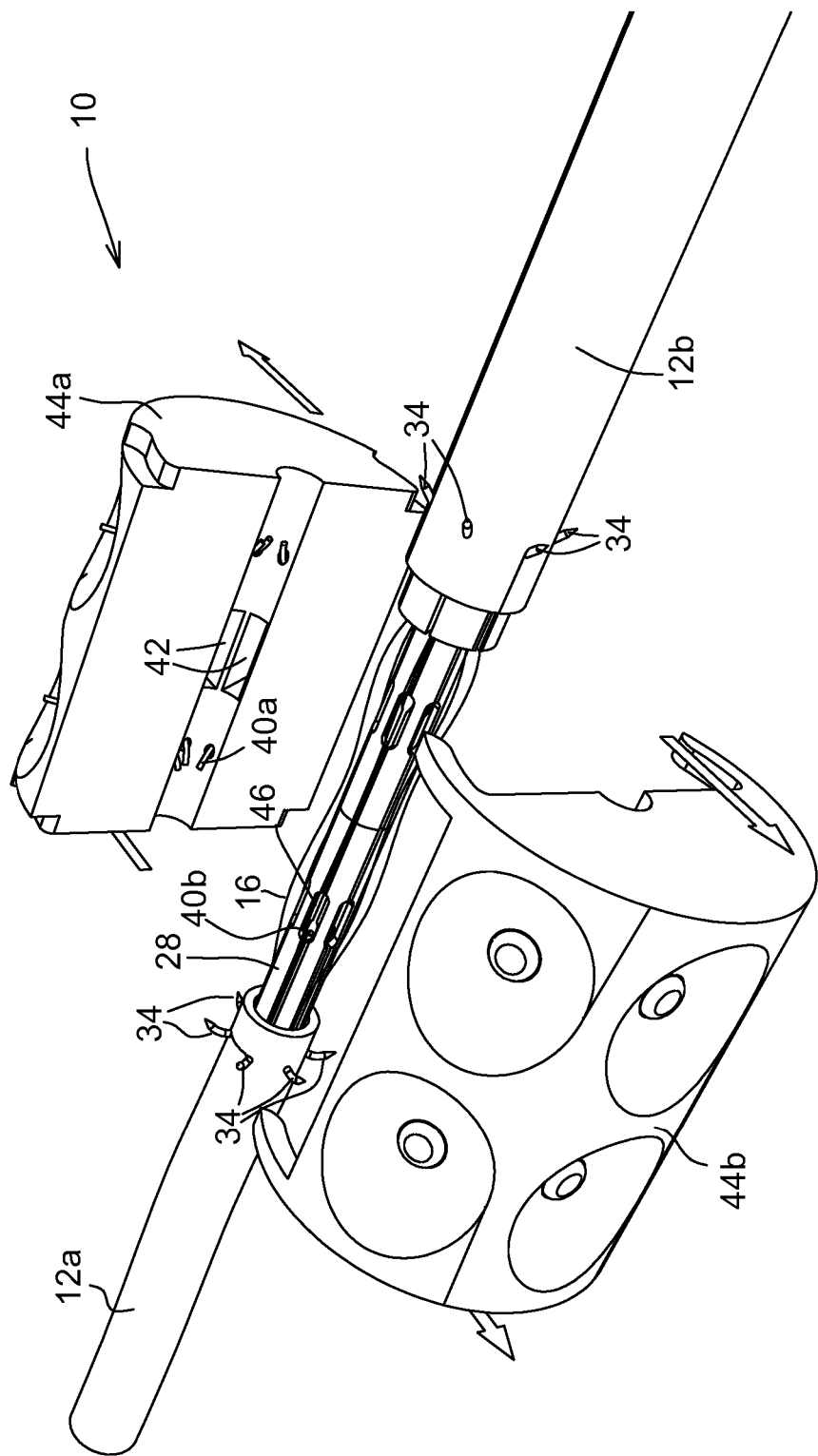
FIG. 3 schematically illustrates a perspective view of the anastomosis suturing device partially disassembled, according to an embodiment of the present invention.

Upon connecting anastomosis suturing device 10 to blood vessels 12a and 12b, the physician may operate a needle activator 36 (FIG. 1), for example, by depressing a button 36a (FIG. 2) to cause needle extender 40a to push needle driver 40b and force needle 34a to protrude through needle slot 30. Needle 34a may protrude through needle slot 30 at least a minimum distance to pierce through a wall of the blood vessel from the inside to the outside of the blood vessel and allow the physician to grasp the needle and/or an end of suture 16 attached to the needle. In a typical anastomosis procedure, the physician may sequentially operate on each needle activator 36 to pass needles 34 (FIG. 1) through the walls of blood vessels 12a and 12b, for example by sequentially depressing buttons 36a-36d (FIG. 2) to sequentially pass needles 34a-34d through the walls of blood vessels 12a and 12b. In FIG. 3 may be seen an exemplary scenario of needles 34 protruding through blood vessels 12a and 12b.

Figure 4:
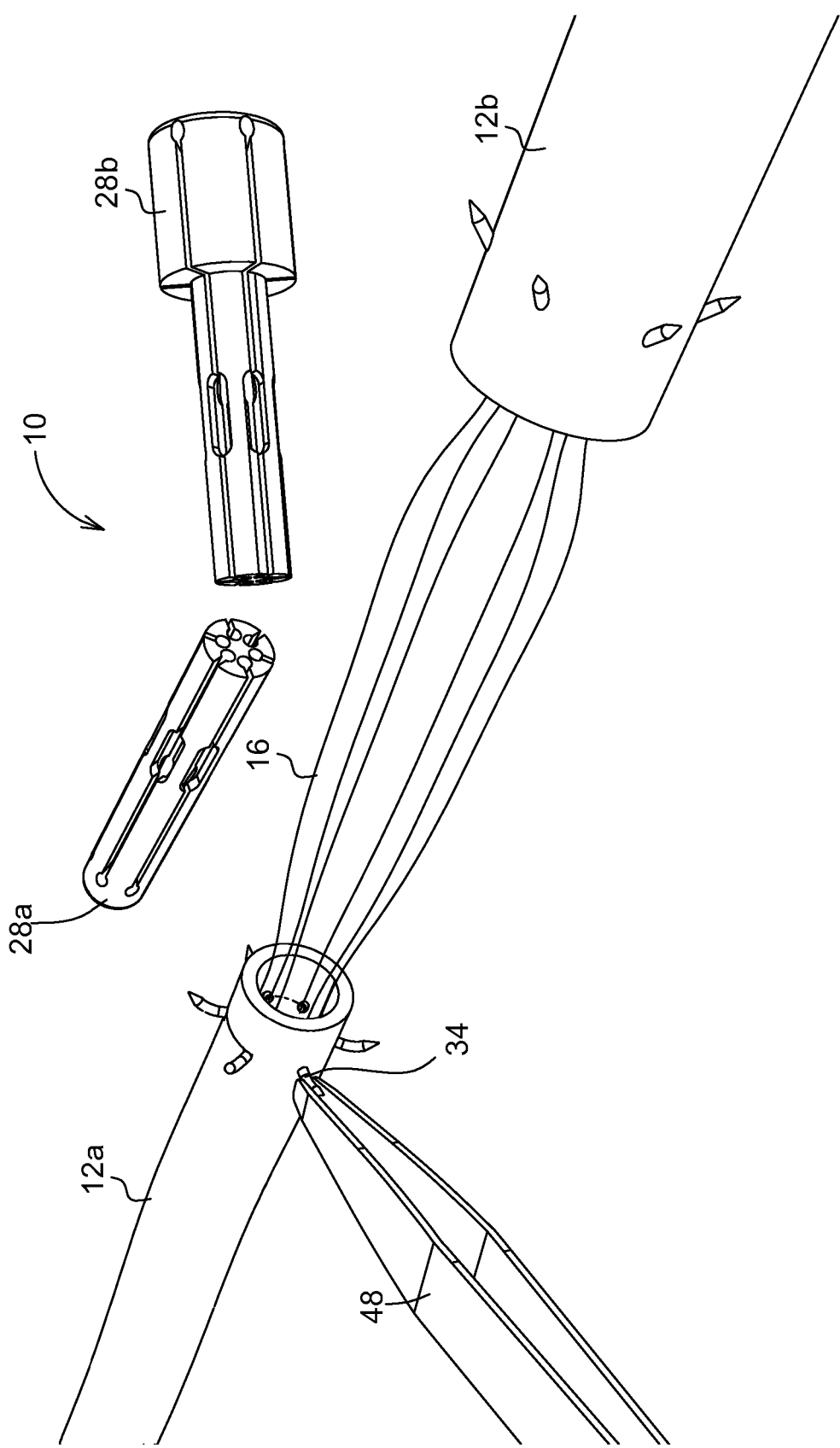
FIG. 4 schematically illustrates a perspective view of the anastomosis suturing device having been dismantled and disconnected from two tubular bodies of living creatures, according to an embodiment of the present invention.

Once needles 34 have been passed through the wall of blood vessel 12a and blood vessel 12b, the physician may prepare for removal of anastomosis suturing device 10. This step of the anastomosis procedure may be seen in FIG. 3 and also in FIG. 4 which schematically illustrate perspective views of anastomosis suturing device 10 having been dismantled and disconnected from blood vessels 12a and 12b, according to an embodiment of the present invention.

The physician may first dismantle casing 44 by separating casing section 44a from casing section 44b. Casing sections 44a and 44b may then be removed leaving tubular sections 28a and 28b connected to blood vessels 12a and 12b with needles 34 protruding through the walls to the outside of the blood vessels, as shown in FIG. 3. The physician may then remove tubular section 28a from blood vessel 12a and tubular section 12b from blood vessel 12b, leaving each suture 16 connected at one end to a needle 34 in blood vessel 12a and at an opposing end to a needle 34 in blood vessel 12b. Following removal of tubular sections 12a and 12b, the physician may join blood vessel 12a and blood vessel 12b together and complete the anastomosis procedure, which may include, for example, pulling each needle 34 with surgical tweezers 48 or other suture pulling/tying instrument.

Description of an Exemplary End-to-Side Anastomosis Suturing Device

In the following description of an end-to-side anastomosis suturing device according to the present invention, parts which may be the same as those used in the end-to-end anastomosis suturing device of the present invention may be identified by the same part reference numbers.

Figure 5:
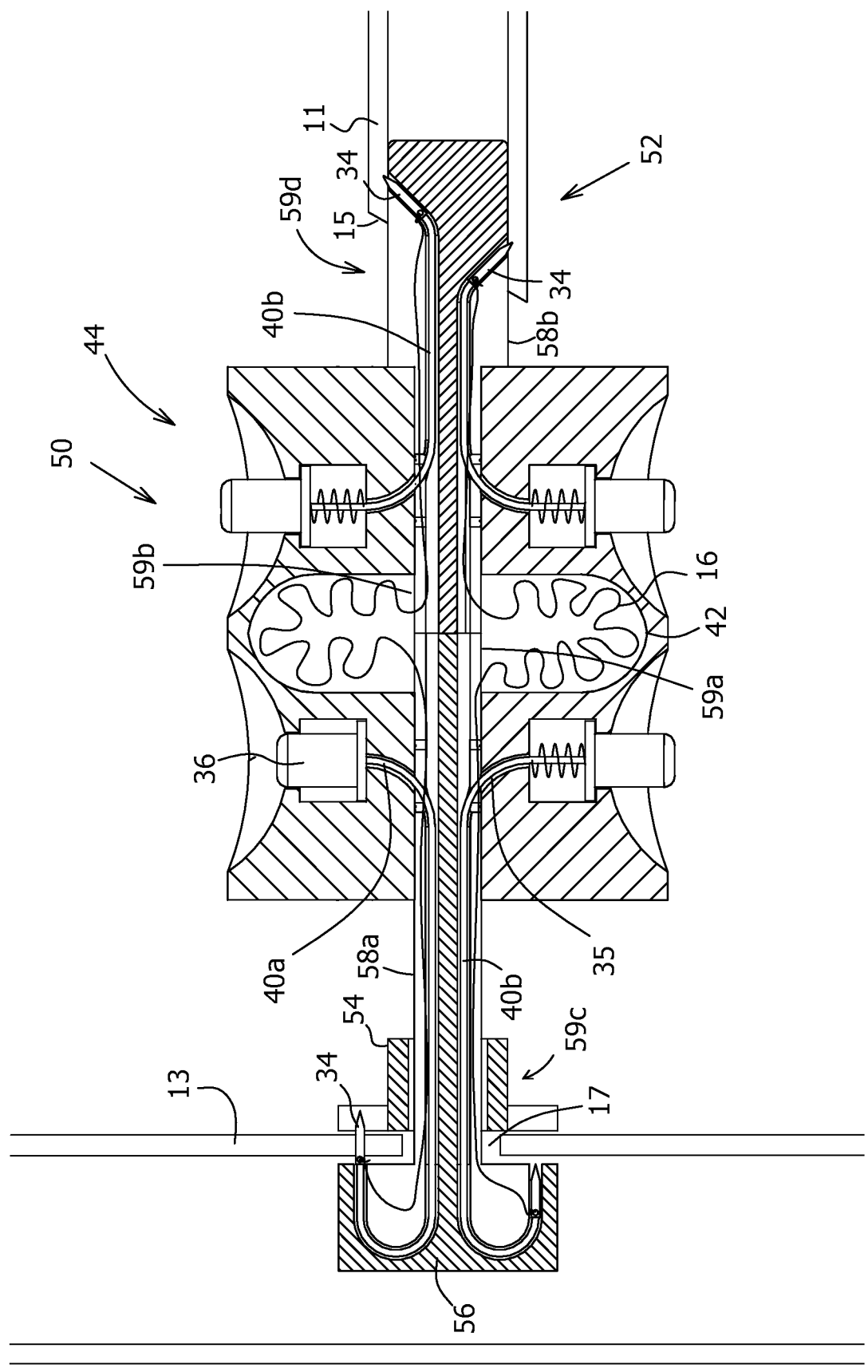
FIG. 5 schematically illustrates a cross-sectional view of an exemplary anastomosis suturing device for use in an end-to-side anastomosis, according to an embodiment of the present invention.
Figure 6:
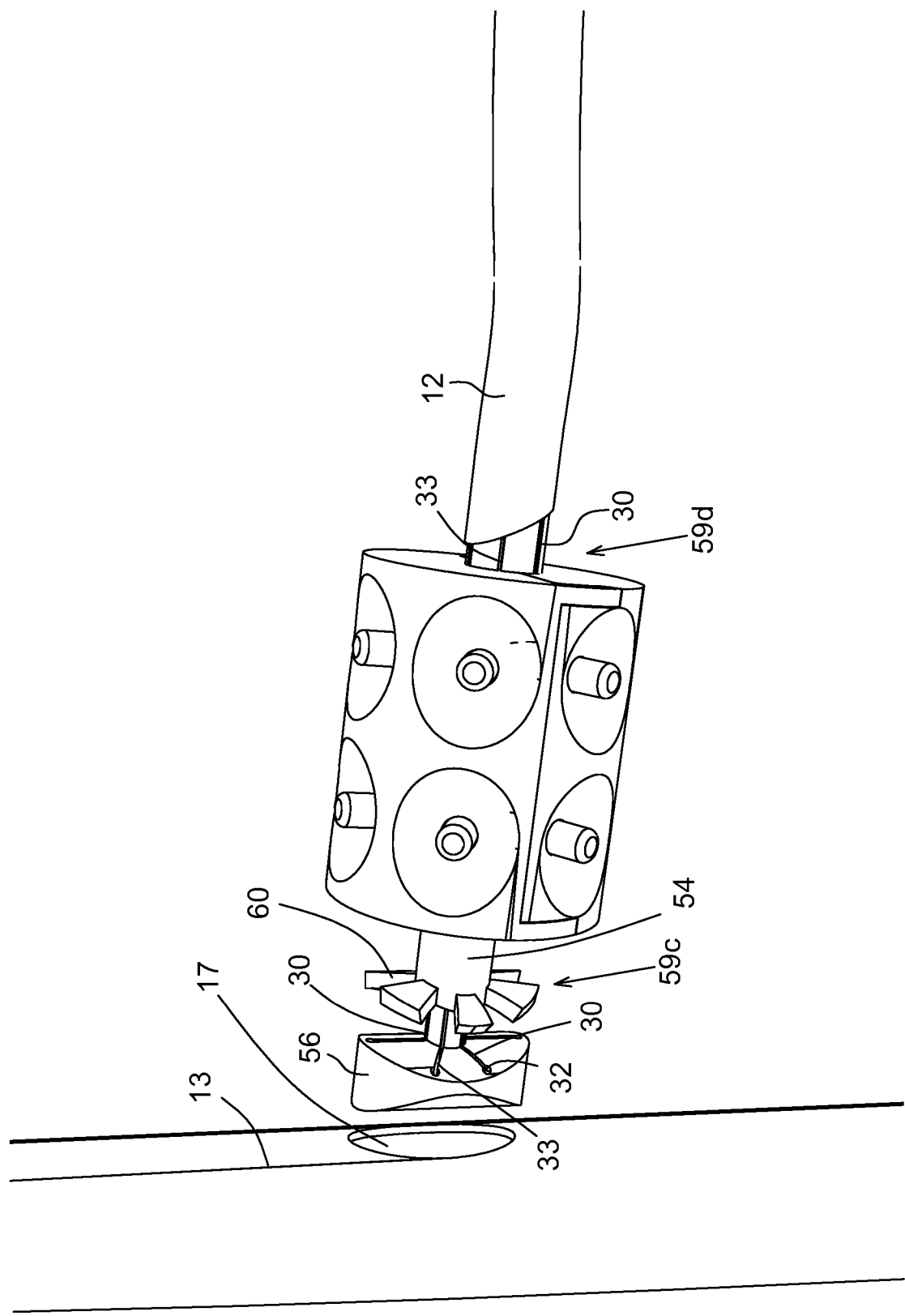
FIG. 6 schematically illustrates a perspective view of the end-to-side anastomosis suturing device being used in an end-to-side anastomosis procedure, according to an embodiment of the present invention.

Reference is now made to FIG. 5 which schematically illustrates a cross-sectional view of an exemplary anastomosis suturing device 50 for use in an end-to-side anastomosis, according to an embodiment of the present invention. Reference is also made to FIG. 6 which schematically illustrates a perspective view of anastomosis suturing device 50 being used in an end-to-side anastomosis procedure, according to an embodiment of the present invention. For exemplary purposes, as shown in FIG. 6, blood vessel 12 having an angled proximal end 15 may be a vein being attached to a neostomy 17 created large blood vessel 13 which may be an artery as part of an arterial bypass procedure or an arteriovenous grafting procedure.

Anastomosis suturing device may include casing 44, a first tubular section 58a, and an opposing second tubular section 58b, both tubular sections partially encased within dismantable casing 44. Casing 44 may include one or more needle activators 36, suture storage cells 42 including sutures 16, conduits 35 and needle drivers 40a, as previously describe in anastomosis suturing device 10. Tubular section 58a may be similar to tubular section 28a in anastomosis suturing device 10 in that it may include needle extenders 40b, suture needles 34, needle slots 30, with slits 33, and needle openings 32 functionally similar to those in anastomosis suturing device 10. Tubular section 58b may be similar to tubular section 28b in anastomosis suturing device 10 with the exception that the length of needle extenders 40b vary according to their position in the tubular section to compensate for angled proximal end 15 in vein 12.

Tubular sections 58a and 58b may include proximal sections 59a and 59b, respectively, enclosed in casing 44, each proximal section having a proximal end which may abut one with the other. Tubular section 58a may additionally include a distal section 59c which protrudes outwards from casing 44 and may be insertable into neostomy 17 in artery 13. Tubular section 58b may additionally include a distal section 59d which protrudes outwards from casing 44 and may be insertable into angled proximal end 15 in vein 11. Distal section 59d may be similar to distal section 29d in anastomosis suturing device 10 with the exception that the lengths of needle slots 30 and the location of needle openings 32 may be different according to their position to compensate for angled proximal end 15 in vein 12.

Distal section 59c may include a distal end 56 which may be insertable through neostomy 17 into an interior of artery 13 and which is shaped to allow suture needles 34 to pierce the walls of the artery peripherally surrounding the neostomy from inside the artery to the outside. The shape of distal end 56 should allow its insertion through neostomy 17 without causing damage to surrounding tissue including to that in the periphery of the opening. A preferable shape may be a mushroom shape, an umbrella shape or other shape having rounded edges as may be appreciated from FIGS. 5 and 6. Additionally, the shape of distal end 56 and an arrangement of the needle slots 30 and needle openings 32 in the proximal end may allow suture needles 34 to protrude through the wall of artery 13 surrounding neostomy 17 from a direction substantially perpendicular to the wall. Alternatively, the arrangement of needle slots 30 and needle openings 32 in distal end 56 may allow suture needle 34 protrusions through the wall at a slanted angle.

Distal section 59c may additionally include a clamp 54 to hold distal end 56 in position around neostomy 17 and to provide support to the distal end and to the wall tissue surrounding the neostomy during driving of suture needles 34 through the wall of artery 13. Clamp 54 may include a circular shape and may be positioned around neostomy 17 on the exterior of the wall of artery 13 to provide sufficient clamping force to hold distal end 56 in place without damaging the wall tissue surrounding the neostomy. Clamp 54 may rest on distal section 59c and its position may be slidably adjusted along the distal section to allow adjusting the clamping force exerted on the wall tissue. Alternatively, clamp 54 may have a predetermined fixed position on distal section 59c to apply a predetermined clamping force on the wall tissue. Clamp 54 may additionally be made of a magnetic material which may apply the clamping force by attracting a metallic proximal end 56 through the wall tissue.

Clamp 54 may include slots 60 which may be aligned on the exterior of the artery wall with needle openings 32 in distal end 56 on the opposite side (interior) of the artery wall. Slots 60 may allow suture needles 34, when penetrating through the artery wall, to protrude into the cavity formed by the slot, and may allow the physician to access (pull) the suture needles and sutures without having to extract distal end 56 from inside artery 13.

Slots 60 may be peripherally distributed around clamp 54 at predetermined positions corresponding to the positions of needle openings 32, or alternatively, may be manually adjustable to allow the physician to accommodate the slots to the position of needle openings 32. For example, to allow manual adjustment of the location of slots 60, clamp 54 may be fitted with one or more covers having slots which may be rotated by the physician to correspond with the position of needle openings 32.

Anastomosis suturing device 50, similarly to anastomosis suturing device 10, may be fabricated of a metal and/or a plastic material which may be subject to sterilization procedures and other clinical cleansing procedures routinely used for surgical instruments including those used for performing an anastomosis. It may be a reusable device or alternatively, a disposable single-use device.

Similarly to anastomosis suturing device 10, anastomosis suturing device 50 may come in various configurations with tubular sections 58a and 58b prefitted in casing 44. Additionally or alternatively, similar to anastomosis suturing device 10, anastomosis suturing device 50 may be part of a kit which may include a replaceable casing 44 and different interchangeable tubular sections 58a and 58b which may be interchanged by the physician depending on the type of anastomosis.

In the figures and/or description herein, the following reference numerals have been mentioned:

| PART REF NO. | PART IDENTIFICATION NAME |
| --- | --- |
| 10 | Anastomosis Suturing Device |
| 11 | Blood Vessel (Vein) |
| 12a | Blood Vessel |
| 12b | Blood Vessel |
| 13 | Large Blood Vessel (Artery) |
| 15 | Angled Proximal End |
| 16 | Suture |
| 17 | Neostomy |
| 28a | First Tubular Section |
| 28b | Second Tubular Section |
| 29a | Proximal Section |
| 29b | Proximal Section |
| 29c | Distal Section |
| 29d | Distal Section |
| 30 | Needle Slots |
| 32 | Needle Opening |
| 33 | Slit |
| 34 | Suture Needle |
| 34a | First Suture Needle |
| 34b | Second Suture Needle |

| PART REF NO. | PART IDENTIFICATION NAME |
| --- | --- |
| 34c | Third Suture Needle |
| 34d | Fourth Suture Needle |
| 35 | Conduit |
| 36 | Needle Activator |
| 36a | First Needle Activator |
| 36b | Second Needle Activator |
| 36c | Third Needle Activator |
| 36d | Fourth Needle Activator |
| 40a | Needle Driver |
| 40b | Needle Extender |
| 42 | Suture Storage Cell |
| 44 | Casing |
| 44a | Casing Section |
| 44b | Casing Section |
| 54 | Clamp |
| 56 | Distal End |
| 58a | Tubular Section |
| 58b | Tubular Section |
| 59a | Proximal Section |
| 59b | Proximal Section |
| 59c | Distal Section |
| 59d | Distal Section |
| 60 | Slots |

The foregoing description and illustrations of the embodiments of the invention has been presented for the purposes of illustration. It is not intended to be exhaustive or to limit the invention to the above description in any form.

Any term that has been defined above and used in the claims, should to be interpreted according to this definition.

The reference numbers in the claims are not a part of the claims, but rather used for facilitating the reading thereof. These reference numbers should not be interpreted as limiting the claims in any form.

The invention claimed is:

1. An anastomosis suturing device comprising:
   a dismantlable casing;
   a first tubular section comprising a proximal section encased in said casing and a distal section insertable in a tubular body of a living creature;
   a second tubular section comprising a proximal section encased in said casing and a distal section insertable in a tubular body of said living creature; and
   at least two suture needles (34),
   wherein said casing comprises:
   at least two buttons (36), each configured to be pressed perpendicularly to a longitudinal axis of at least one of said tubular bodies of said living creature, for pushing at least one of said suture needles (34) to protrude through one of the tubular bodies of the living creature.

2. The anastomosis suturing device according to claim 1 wherein said casing comprises at least one suture storage cell.

3. The anastomosis suturing device according to claim 1 wherein said casing comprises at least one needle driver operable to push a needle extender in said first or second tubular section.

4. The anastomosis suturing device according to claim 1 wherein said casing comprises a first casing section and a second casing section.

5. The anastomosis suturing device according to claim 1 wherein said first tubular section and said second tubular section each comprise at least one needle slot to slidingly accommodate a needle extender.

6. The anastomosis suturing device according to claim 5 wherein said at least one needle slot in said first and second tubular sections comprises a slit to accommodate a suture.

7. The anastomosis suturing device according to claim 1 wherein said first tubular section and said second tubular section each comprise at least one needle extender to push on at least one of said suture needles.

8. The anastomosis suturing device according to claim 1 wherein said first tubular section and said second tubular section each comprise at least one needle opening to allow protruding of at least one of said suture needles.

9. The anastomosis suturing device according to claim 1 wherein said first tubular section and said second tubular section each comprise at least one of said suture needles.

10. The anastomosis suturing device according to claim 1 wherein said first tubular section and said second tubular section comprise distal ends having different diameters.

11. The anastomosis suturing device according to claim 1 wherein said first tubular section and said second tubular section comprise distal ends having same diameters.

12. The anastomosis suturing device according to claim 1 wherein the device is configured to be used for an end-to-end anastomosis.

13. The anastomosis suturing device according to claim 12 wherein the end-to-end anastomosis comprises two veins.

14. The anastomosis suturing device according to claim 13 wherein the end-to-end anastomosis comprises an artery and a vein.

15. The anastomosis suturing device according to claim 1 wherein the device is configured to be used for an end-to-end anastomosis.

16. The anastomosis suturing device according to claim 1 wherein the device is configured to be used for an side-to-side anastomosis.

* * * * *